United States Patent
Estrine et al.

(10) Patent No.: US 8,709,978 B2
(45) Date of Patent: Apr. 29, 2014

(54) HERBICIDE COMPOSITION HAVING IMPROVED EFFECTIVENESS, METHOD OF PREPARATION AND USE

(75) Inventors: Boris Estrine, Nanteuil la Forët (FR); Sinisa Marinkovic, Avançons (FR); Philippe Kuenemann, Sartrouville (FR); Corinne Lajoie, Lavannes (FR); Antoine Paris, Douai la Fontaine (FR); Cédric Ernenwein, Nouvion le Vineux (FR)

(73) Assignees: Agro Industrie Recherches et Developpements (A.R.D.), Pomacle (FR); Phyteurop, Levallois-Perret (FR)

( * ) Notice: Subject to any disclaimer, the term of this patent is extended or adjusted under 35 U.S.C. 154(b) by 13 days.

(21) Appl. No.: 13/552,944

(22) Filed: Jul. 19, 2012

(65) Prior Publication Data

US 2013/0035234 A1    Feb. 7, 2013

(51) Int. Cl.
*A01N 37/10* (2006.01)
*A01N 39/02* (2006.01)

(52) U.S. Cl.
USPC ............ 504/144; 504/145; 504/323; 504/324

(58) Field of Classification Search
None
See application file for complete search history.

(56) References Cited

FOREIGN PATENT DOCUMENTS

| WO | WO 92/01376 A1 | 2/1992 |
|----|----|----|
| WO | WO 2010/003889 A1 | 1/2010 |
| WO | WO 2010/086437 A2 | 8/2010 |
| WO | WO 2011/039172 A2 | 4/2011 |
| WO | WO 2011/082162 A1 | 7/2011 |

OTHER PUBLICATIONS

French Search Report (FR 1102420—dated Mar. 2, 2012—3 pages).

*Primary Examiner* — Alton Pryor
(74) *Attorney, Agent, or Firm* — Renner, Kenner, Greive, Bobak, Taylor & Weber

(57) ABSTRACT

Herbicide composition containing at least one herbicide from the family of phenoxyalkanoic acids in acid form and/or a benzoic acid derivative, and at least one solvent or oil, characterized in that the composition includes at least one surfactant and contains from 0 to 5% by mass of water.

14 Claims, No Drawings

HERBICIDE COMPOSITION HAVING IMPROVED EFFECTIVENESS, METHOD OF PREPARATION AND USE

The present invention relates to compositions containing at least one herbicide from the family of phenoxyalkanoic acids and/or derivatives of benzoic acid, methods for preparing said compositions and their use for controlling or destroying weeds in lower herbicide doses than the doses generally administered.

Phenoxyalkanoic acids are a family of selective herbicides which are very widely used throughout the world. Members of this group of molecules (see formulae below) include at least one chlorine atom linked at C4 to a benzene ring and another chlorine atom or a $CH_3$ group at C2. Sometimes a third chlorine atom is present at C5 in the aromatic ring.

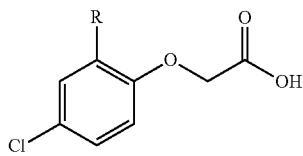

(a) R = $CH_3$; MCPA
(b) R = Cl; 2,4D

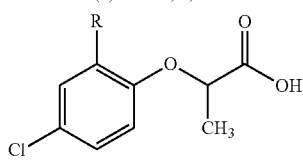

(a) R = $CH_3$; Mecoprop
(b) R = Cl; Dichlorprop

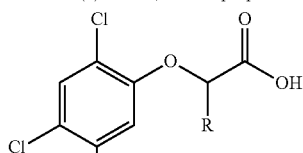

(a) R = H; 2,4,5 T
(b) R = $CH_3$; Fenoprop

Herbicides derived from benzoic acid, such as Dicamba or 2,3,6-TBA (see figure below), can be used alone or mixed with phenoxyalkanoic acids, in particular to extend the range of herbicide activity.

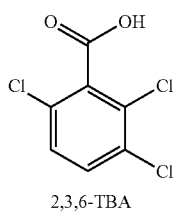
2,3,6-TBA

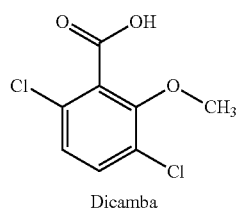
Dicamba

The most commonly encountered forms are amine salts, in particular ethanolamine, triisopropyl or dimethylamine salts or more rarely sodium or potassium salts, which are soluble in water and formulated with or without surfactant. Esters, in particular ethyl, butoxyethanol, butyl, amyl, isobutyl, octyl, isooctyl, butyl glycol, octyl glycol esters, which are insoluble in water and formulated as emulsifiable concentrates (EC) or emulsions (EW) are also available commercially. These latter examples are generally more phytotoxic than the equivalent salts and hence less selective. Esters also present problems of volatility and drift during pulverisation and hence of toxicity for users along with the risk of destruction of adjacent crops and/or environmental contamination.

The penetration of herbicides through the plant cuticles is encouraged by weakly polar molecules solubilised in an oil or solvent. The ester and acid forms formulated as an EC, EW or microemulsion (ME) are thus more phytotoxic than the equivalent salts solubilised in water. The risk with the first forms is that all or part of the selectivity is lost. The loss of selectivity is generally indicated by symptoms of phytotoxicity in agricultural plants that have been treated and by falls in yield.

It has been found that the use of herbicides from the family of phenoxyalkanoics or from the family of benzoic acid derivatives in free acid forms sprayed in lower doses than the generally recognised doses allows effectiveness to be retained in the fight against weeds whilst maintaining selectivity for the treated agricultural plants if the selected herbicide or herbicides are formulated in accordance with the present invention. The composition according to the invention contains less than 5% by mass of a herbicide from a family other than the aforementioned two families. Preferably it contains none at all. In particular it is free from N-1-naphthylphthalamic acid, a salt thereof or an ester salt thereof, in contrast to the formulations described in WO2010/086437, in which naptalam is a mandatory constituent and in which although the acid form is mentioned as a simple nomenclature procedure, only salts are used in the examples.

A further aspect of the present invention relates to the use of inert ingredients having low environmental impacts and low toxicity on the one hand and to the use of herbicides in reduced doses on the other, presenting important technical, economic and environmental advantages along with a lesser danger, which the present invention seeks to provide.

The present invention thus relates to compositions containing at least one herbicide from the family of phenoxyalkanoic acids and/or from the family of benzoic acid derivatives in acid form, methods for preparing said compositions and their use for controlling or destroying weeds in lower herbicide doses than the doses generally administered.

The present invention more particularly relates to compositions containing at least one herbicide from the family of phenoxyalkanoic acids and/or from the family of benzoic acid derivatives in free acid form formulated with inert ingredients having low environmental impacts, methods for preparing said compositions and their use for controlling or destroying weeds in lower herbicide doses than the doses generally administered.

The present invention relates still more particularly to the formulation of emulsifiable concentrates containing at least one herbicide from the family of phenoxyalkanoic acids and/or from the family of benzoic acid derivatives in acid form, at least one organic solvent or an oily phase and at least one surfactant. The composition according to the invention preferably contains less than 5% by mass of water, preferably less than 3% by mass and more preferably less than 0.1%. Ideally it is anhydrous.

The preferred phenoxyalkanoic acids are 2,4-D (2,4-dichlorophenoxyacetic acid), 2,4-DB (2-(2,4-dichlorophenoxy)butyric acid), dichlorprop ((RS)-2-(2,4-dichlorophenoxy)propionic acid), dichlorprop-P ((R)-2-(2,4-dichlorophenoxy)propionic acid), MCPA (4-chloro-o-tolyloxyacetic acid), MCPB (4-(4-chloro-o-tolyloxy)butyric acid), mecoprop ((RS)-2-(4-chloro-o-tolyloxy)propionic acid), mecoprop-p ((R)-2-(4-chloro-o-tolyoxy)butyric acid). The preferred acid derived from benzoic acid is Dicamba (3,6-dichloro-o-anisic acid).

The organic solvents or their oily phases are chosen for their capacity to solubilise and prevent crystallisation of the selected herbicides, even at temperatures below 4° C.

Although synthetic solvents may be suitable, preferred solvents or oily phases are chosen from solvents synthesised with at least one raw material of vegetable origin or obtained by a process involving a fermentation stage, or obtained by extraction, separation and purification of a vegetable biomass. As a general rule the solvents are chosen from those having an acceptable environmental profile. Acceptable environmental profile is understood to mean, inter alia, products that are readily biodegradable aerobically and/or anaerobically and have low ecotoxicity for aquatic and terrestrial environments. The solvents are chosen from the class of terpenes, esters of acids obtained by fermentation or biodegradable esters, alcohols obtained by fermentation or by synthesis and partial derivatives thereof or derivatives of vegetable oils.

Of the terpenes, linear or cyclic monoterpenes are preferred, in particular limonene, alpha-pinene, beta-pinene, terpinolene, dihydromyrcene, myrcene, paracymene, linear or cyclic sesquiterpenes such as farnesene, pine resin esters such as glycerol or pentaerythritol esters, terpene alcohols such as menthol, terpineol, isoborneol, nerol, citronellol, geraniol, myrcenol, linalool and farnesol, purified or mixed together.

Of the fermentative acid esters, preference is given to lactic acid esters, such as ethyl lactate, methyl lactate, propyl lactate, butyl lactate, pentyl lactate, amyl lactate, 2-methylbutyl lactate, hexyl lactate, 2-ethylhexyl lactate, isopropyl lactate, isooctyl lactate, octyl lactate, isodecyl lactate, decyl lactate, esters of lactic acid and C12 to C24 Guerbet alcohols, succinic acid diesters such as dimethyl succinate, diethyl succinate, diisopropyl succinate, dibutyl succinate, diisoamyl succinate, di-2-methylbutyl succinate, dihexyl succinate, di-2-ethylhexyl succinate, dioctyl succinate, diisooctyl succinate, dinonyl succinate, diisononyl succinate, didecyl succinate, diisodecyl succinate, equivalent monoesters, esters of succinic acid and C12 to C24 Guerbet alcohols, adipic acid diesters, in particular dimethyl adipate, diethyl adipate, diisopropyl adipate, dibutyl adipate, diisoamyl adipate, 2-methylbutyl adipate, dihexyl adipate, di-2-ethylhexyl adipate, dioctyl adipate, diisooctyl adipate, dinonyl adipate, diisononyl adipate, didecyl adipate, diisodecyl adipate, equivalent monoesters, esters of adipic acid and C12 to C24 Guerbet alcohols, glutaric acid diesters and in particular dimethyl glutarate, diethyl glutarate, diisopropyl glutarate, dibutyl glutarate, diisoamyl glutarate, 2-methylbutyl glutarate, dihexyl glutarate, di-2-ethylhexyl glutarate, dioctyl glutarate, diisooctyl glutarate, dinonyl glutarate, diisononyl glutarate, didecyl glutarate, diisodecyl glutarate, equivalent monoesters, esters of glutaric acid and C12 to C24 Guerbet alcohols, mono-, di- or triesters of citric acid, in particular trimethyl citrate, triethyl citrate, acetyl triethyl citrate, tripropyl citrate, tributyl citrate, triamyl citrate, tri-2-methylbutyl citrate, trihexyl citrate, triethylhexyl citrate, acetyl triethylhexyl citrate, acetyl trioctyl citrate, trioctyl citrate, trinonyl citrate, acetyl trinonyl citrate, tridecyl citrate, triisodecyl citrate, tricapryiyl citrate, esters of citric acid and C12 to C24 Guerbet alcohols, fumaric acid esters such as dimethyl fumarate, diethyl fumarate, diisopropyl fumarate, dibutyl fumarate, diamyl fumarate, di-2-methylbutyl fumarate, dihexyl fumarate, di-2-ethylhexyl fumarate, dioctyl fumarate, diisooctyl fumarate, dinonyl fumarate, diisononyl fumarate, didecyl fumarate, diisodecyl fumarate, equivalent monoesters, esters of fumaric acid and C12 to C24 Guerbet alcohols, malic acid esters such as dimethyl malate, diethyl malate, diisopropyl malate, dibutyl malate, diamyl malate, di-2-methylbutyl malate, dihexyl malate, di-2-ethylhexyl malate, dioctyl malate, diisooctyl malate, dinonyl malate, diisononyl malate, didecyl malate, diisodecyl malate, equivalent monoesters, esters of malic acid and C12 to C24 Guerbet alcohols, acetic acid esters such as ethyl acetate, propyl acetate, isopropyl acetate, butyl acetate, amyl acetate, 2-methyl butanol acetate, hexyl acetate, 2-ethylhexyl acetate, octyl acetate, isooctyl acetate, nonyl acetate, isononyl acetate, decyl acetate, isodecyl acetate, esters of acetic acid and C12 to C24 Guerbet alcohols.

Other preferred esters are the esters derived from vegetable oils, in particular esters of colza, sunflower, soya, linseed, copra, palm, castor, groundnut, walnut, olive, maize and coconut oil, in ethyl, methyl, propyl, isopropyl, butyl, isobutyl, amyl, 2-methylbutyl, hexyl, 2-ethylhexyl, octyl, isooctyl, nonyl, isononyl, decyl, isodecyl or glycerol form or esterified with C12 to C24 Guerbet alcohols.

Purified fatty acid esters, in particular caproic, caprylic, capric, lauric, myristic, myristoleic, palmitic, palmitoleic, stearic, oleic, ricinoleic, linoleic, arachidic, gadoleic, behenic, erucic, lignoceric acid esters, in ethyl, methyl, propyl, isopropyl, butyl, isobutyl, amyl, 2-methylbutyl, hexyl, 2-ethylhexyl, octyl, isooctyl, nonyl, isononyl, decyl, isodecyl, palmetic, cetyl, isocetyl, oleic, stearic, isostearic, linoleic, arachidic or behenic form or esterified with C12 to C28 Guerbet alcohols, pure or mixed together.

Of the alcohols and alcohol derivatives, preference is given to ethanol, isopropanol, butanol, amyl alcohols, 2-methyl butanol, hexanol, 2-ethylhexanol, octanol, isooctanol, decanol, isodecanol, dodecanol, C12 to C24 Guerbet alcohols, pure or mixed together, glycerol and partial glycerol derivatives, in particular polyglycerol and polyglycerol esters such as polyglycerol polyricinoleate, glycerol esters such as glycerol monooleate, glycerol carbonate, erythritol and derivatives thereof, in particular pentaerythritol monooleate, pentaerythritol tetraisostearate, pentaerythritol tetraoleate, diols such as ethylene glycol, 1,2-propanediol, 1,3-propanediol, 2,3-butanediol, 1,2-butanediol, 1,4-butanediol, 1,3-butanediol, 1,5-pentanediol, 1,2-pentanediol, 2-ethylhexane-1,3-diol, 1,8-octanediol, 2-methyl-2,4-pentanediol, diethylene glycol, dipropylene glycol.

Natural oils can also be used, and in particular colza, sunflower, soya, linseed, copra, palm, castor, groundnut, walnut, olive, maize, coconut, sweet almond, argan, common sea buckthorn, avocado, wheat, borage, calendula, callophyllum, cottonseed, jojoba, macadamia nut, pine, grape seed, sesame, peach kernel and galip nut oils and caprylyl/capric acid triglycerides.

The purpose of the emulsifying system of the preparation according to the invention is to render the non-water-soluble molecules of the preparation dispersible or emulsifiable. It consists of one or more surfactants solubilised or non-solubilised in water or an external solvent.

The surfactants are selected for their capacity to be soluble in the lipophilic phase constituted by the selected herbicide or herbicides in acid form and the selected solvent(s), as well as for their capacity to render the ingredients of the preparation compatible and to allow them to be dispersed or emulsified once diluted in water. This dispersion or emulsification generally takes place without an excessive input of energy, either at ambient temperature or at a temperature below 95° C. or even below 50° C., and without the use of special mixers, such as a colloid mill, high-pressure homogeniser, the use of specific stirrer blades such as those provided with a rotor and stator and rotated by means of a powerful motor, or without the use of ultrasound. As this dispersion or emulsification is performed easily, it is generally described as a spontaneous or instantaneous dispersion or emulsification performed by gentle stirring or movement of the liquid in a pump. This dispersion or emulsification is generally performed in moderately hard to hard water, generally between 15 and 50° C. The rate of dilution of the composition in water is chosen so as to guarantee the effectiveness of the herbicide(s) of the composition whilst retaining if necessary the selectivity of the herbicide(s) of the preparation. CIPAC method MT 36 at a dilution of 5% in water having a hardness of 342 ppm (Ca2+/Mg2+ ratio of 4/1) was used to select the emulsifying system. This method involves diluting 5 ml of the preparation in 100 ml of standard water to give an aqueous emulsion after shaking the graduated measuring cylinder used for the mixture. The stability of this emulsion is then determined by measuring the volume of salted-out oil or of creamed phase after resting for 30 minutes, 2 hours and 24 hours. The capacity of the emulsifying system to re-emulsify the phases present after this 24-hour period is also assessed.

The surfactants of the emulsifying system of the preparation of the invention are chosen from those capable of keeping the composition stable over time and at generally accepted temperatures, i.e. between 4° C. and 45° C., and enabling the system to remain stable even after successive freeze-thaw cycles, generally between −12° C. and the laboratory temperature, and allowing a spontaneous and stable emulsification in accordance with the test described by CIPAC method MT 36.

The emulsifying system can for example be chosen from those described in the document WO 2005/110588 A1 in the applicant's name.

More particularly, the emulsifying system contains at least one surfactant of formula ROXn in which R is a linear or branched aliphatic group, saturated or unsaturated, having 6 to 22 carbon atoms, preferably 8 to carbon atoms, X is a pentose radical, more particularly a xylose radical, and n is between 1 and 3, more particularly between 1 and 1.8, and represents the degree of oligomerisation of the sugar.

The aforementioned emulsifying system can be used on its own or mixed with a non-ionic, anionic, cationic or amphoteric co-surfactant. A non-ionic or anionic co-surfactant is preferably used.

Of the non-ionic co-surfactants, preference is given to ethoxylated or non-ethoxylated sorbitan esters, such as sorbitan monolaurate, sorbitan monopalmitate, sorbitan monooleate, sorbitan monostearate, sorbitan trioleate, sorbitan tristearate, sorbitan sesquioctanoate, sorbitan sesquioleate, ethoxylated derivatives of the Tween series such as polyethoxylated sorbitan monolaurate having 20 ethoxylate units (Tween 20), polyethoxylated sorbitan monooleate having 20 ethoxylate units (Tween 80), polyethoxylated sorbitan monostearate having 20 ethoxylate units (Tween 60), glycerol or polyglycerol esters such as glyceryl monooleate, glyceryl monococoate, glyceryl monolaurate, glyceryl monoisostearate, glyceryl dioleate, glyceryl monoricinoleate, polyglycerol polyricinoleate, polyglycerol polyisostearate, polyglycerol polyoleate, polyglycerol polylaurate, PEG-7 glyceryl cocoate, PEG-12 glyceryl laurate, PEG-20 glyceryl stearate, PEG-100 glyceryl stearate, polyethylene glycol esters such as PEG-200 monooleate, PEG-400 diisostearate, PEG-400 dioleate, PEG-400 diricinoleate, PEG-400 monolaurate, PEG-400 monooleate, PEG-400 monostearate, PEG-600 dioleate, PEG-600 distearate, PEG-600 monooleate, PEG-1500 monostearate, ethoxylated fatty alcohols and more particularly those having an HLB between 4 and 12 such as stearyl alcohol having 2 to 10 ethoxylated units, oleic acid having 2 to ethoxylated units, cetyl alcohol having 2 to 10 ethoxylated units, C13 to C15 alcohols having 2 to 10 ethoxylated units, lauric alcohol having 2 to 8 ethoxylated units, decyl alcohol having 2 to 8 ethoxylated units, polyethoxylated fatty acid esters such as colza methyl ester having 7 ethoxylated units, polyethoxylated vegetable oils such as hydrogenated or non-hydrogenated castor oil having 10 ethoxylated units, sucrose esters such as sucrose mono- or polylaurate, sucrose mono- or polymyristate, sucrose mono- or polypalmitate, sucrose mono- or polystearate.

Preferred anionic co-surfactants are for example sodium stearoyl lactate, glyceryl stearate citrate, glyceryl stearate lactate, sodium lauroyl, cocoyl, myristoyl, oleoyl or stearoyl glutamate, sodium lauroyl, cocoyl, myristoyl, oleoyl or stearoyl sarcosinate, sulfosuccinic acid esters such as sodium diamyl, dihexyl, di-2-ethylhexyl, dioctyl, ditridecyl, diisodecyl sulfosuccinate, ethoxylated derivatives such as laureth disodium sulfosuccinate, potassium, sodium or diethanolamine salts of fatty acid such as potassium oleate, sodium palmitate, potassium olivate, potassium, sodium or diethanolamine salts of phosphoric esters such as potassium cetyl phosphate, anionic derivatives of alkyl polyglucosides such as sodium cocopolyglucose succinate, disodium cocopolyglucose citrate, sodium cocopolyglucose tartrate, sodium lauryl glucose carboxylate, sulfated fatty alcohols such as C12/C14 sodium sulfate alcohol, sulfated ethoxylated fatty alcohols such as lauric alcohol having 4 ethoxylated sulfated sodium or magnesium units.

The content of herbicide(s) from the family of phenoxyalkanoic acids and/or benzoic acid derivative in acid forms in the preparation is between 1 and 95% by mass relative to the total mass of the preparation, preferably between 5 and 60%, more preferably between 10 and 45%, the remainder being made up of the surfactant(s) and solvent(s) or oils, and optionally one or more co-surfactants and more rarely water. The composition according to the invention preferably contains less than 3% by mass of water, preferably less than 1% by mass and more preferably less than 0.1%. Anhydrous compositions are thus preferred.

The proportion of the emulsifying system made up of surfactants and optionally co-surfactants, relative to the solvents or oils, is between 1/0.10 and 1/20, and more generally between 1/0.5 and 1/9, still more generally between 1/1 and 1/8.5.

If present, the co-surfactant(s) represent from 0.1 to 50% of the total mass of the emulsifying system present in the composition, preferably from 1 to 50%, more preferably from 10 to 45%.

The compositions according to the invention thus preferably contain, relative to the total mass of the preparation, from 1 to 65%, and preferably from 10 to 45%, of one or more phenoxyalkanoic acids in acid forms, from 20 to 98%, and preferably from 25 to 85%, of one or more solvents or oils, from 1 to 65%, and preferably from 5 to 45%, of one or more surfactants of formula ROXn, in which R is a linear or branched aliphatic group, saturated or unsaturated, having 8 to 12 carbon atoms, X being a xylose radical and n being a number between 1 and 1.8, and from 0 to 60%, and preferably from 1 to 25%, of one or more non-ionic, anionic, cationic or amphoteric co-surfactants.

The compositions according to the invention can be prepared by one of the following methods.

Non-volatile or scarcely volatile solvents (not classed in the category of VOC products) are mixed together and brought to a temperature of between 0 and 150° C., preferably from 25 to 95° C., more preferably from 35 to 65° C., under mechanical agitation with the aid of a stirrer blade and a motor, or by liquid recirculation via a pump. Once the temperature has stabilised, the herbicide(s), generally in the form of powders or of chopped or pelletised solids, are gradually added to the liquid, either manually or with the aid of a mechanical powder feeder. Once all of the solid has been solubilised in the liquid to form a homogeneous, generally isotropic, liquid, heating is stopped and optionally replaced by cooling to reach a temperature of between 10 and 45° C., preferably between 10° C. and ambient temperature. The other ingredients are then added to the preparation under mechanical agitation until a homogeneous liquid is obtained. The reactor serving as the mixing zone can be open and under atmospheric pressure, or closed and topped with a cooling column serving to condense the vapours formed and under atmospheric pressure or rendered inert with a gas such as nitrogen.

A variant of this method of preparation involves adding all of the liquids, in other words solvents, oils, surfactants and co-surfactants in liquid forms, and stirring the mixture, then adding all of the solids, in other words herbicides in acid forms and solid surfactants and co-surfactants, at a temperature of between 15 and 150° C., preferably between 25 and 95° C., more preferably between 35 and 65° C. Stirring is continued until a homogeneous and optionally isotropic liquid is obtained, before the cooling step is initiated.

A further variant of the above method involves adding all of the ingredients of the preparation in a single step and of keeping the mixture under mechanical agitation and at a temperature of between 15 and 150° C., preferably between 25 and 95° C., more preferably between 35 and 65° C., until a homogeneous and optionally isotropic liquid is obtained. The product is then cooled by stopping heating and returning it to ambient temperature or with the aid of a cryostat.

The herbicide compositions according to the invention are applied to target plants so as to control their growth or to cause their degeneration and death. The methods of application are those conventionally used in agriculture, arboriculture, viticulture, market gardening, gardening or by local authorities. The herbicide compositions can be applied directly to the target plants or following dilution in water or an aqueous phase at a concentration guaranteeing the effectiveness of the treatment whilst also guaranteeing adequate safety for users or consumers and without risk to the environment. The amount of water added represents from 75 to 99.999%, preferably from 95 to 99.9%, of the total mass of the preparation. Other herbicide, fungicide, insecticide, elicitor, growth regulator or nutrient compositions or other inert ingredients (or extemporaneous additives) can be added to the preparation (mixture) prior to its use.

The preparations can be sprayed onto the plants by means of a manual spray gun or by wheeled (tractor, quad bike, car, etc.) or airborne (aeroplane, helicopter, etc.) mechanical means. The spraying quality is ensured by the judicious choice of spray nozzles, the pressure applied to the liquid and the rate of flow of the spraying system onto the crop.

In the case of large-scale farming (cereals, maize, beet, etc.), the amounts of herbicide mixture that are sprayed are generally from 50 to 1000 liters per hectare, more particularly from 100 to 500 liters per hectare, and still more particularly from 100 to 300 liters per hectare. For the treatment of grassland, lawns or in arboriculture the amounts are generally from 100 to 1000 liters per hectare and more particularly from 200 to 500 liters per hectare.

To ensure the selectivity of the herbicide preparations according to the invention, the herbicide doses applied to the crop are lower than the doses generally used. These generally used doses are dependent on the type of crop or plant, the nature of the herbicide(s) in the preparation, the country or regions of application, the season, the method of application and optionally climatic conditions. The doses and the methods of application can be recommended by the herbicide suppliers, specialist institutes, technical centres, the legislative body of the country in question, professional or consumer associations or agricultural cooperatives. The applicable doses per hectare can vary according to the legislation in force in the country in question and the active ingredients used alone or in combination. By way of example and without intending to be limiting, the compositions according to the invention based on 2,4-D acid can be applied, in grams of herbicide per hectare, at a rate of 8.4 to 840 g/ha, preferably 280 to 560 g/ha in the case of cereals, 12 to 1200 g/ha, preferably 240 to 800 g/ha in the case of maize, 10 to 1000 g/ha, preferably 200 to 667 g/ha in the case of arboriculture, 15 to 1500 g/ha, preferably 300 to 1250 g/ha in the case of lawns and grassland.

In large-scale farming (cereals, maize, beet, etc.) and in arboriculture, the herbicide compositions according to the invention are thus applied at a dose that is reduced by a factor of 1.01 to 1000, more generally by a factor of 1.5 to 100, still more generally by a factor of 1.5 to 10 and still more particularly by a factor of 1.5 to 5 relative to the hitherto recommended dose, depending on the crop or plant to be treated, the method of treatment and climate conditions. For the treatment of grassland or lawns, the herbicide compositions according to the invention are thus applied at a dose that is reduced by a factor of 1.01 to 1000, more generally by a factor of 1.2 to 100, still more generally by a factor of 1.2 to 10 and still more particularly by a factor of 1.2 to 5 relative to the hitherto recommended dose, depending on the crop or plant to be treated, the method of treatment and climate conditions.

The herbicide composition according to the invention can be used to control a large number of different annual or perennial species, depending on the herbicide or herbicides that are present, either immediately or over the long term. By way of example and without intending to be limiting, the table below provides examples of plants that are controlled, according to the herbicides used in the composition:

| Common name | Scientific name | 2,4 D | 2,4 DB | Dichlorprop-P | 2,4-MCPA | 2,4-MCPB | Mecoprop |
|---|---|---|---|---|---|---|---|
| Chamomile (corn, tall, stinking, yellow) | *Anthemis (arvensis, altissima cotula) chamaemelum mixtum* | | | | x | | |
| Mugwort | *Artemisia vulgaris* | x | | | | | |
| Common orache | *Atriplex patula* | x | | | x | x | x |
| Cornflower | *Centaurea cyanus* | x | x | | x | x | |
| Shepherd's-purse | *Capsella bursa pastoris* | x | x | | x | x | x |
| Hairy bittercress | *Cardamine hirsuta* | x | | | | | |
| Sticky mouse-ear | *Cerastium glomeratum* | | | | | | x |

-continued

| Common name | Scientific name | 2,4 D | 2,4 DB | Dichlorprop-P | 2,4-MCPA | 2,4-MCPB | Mecoprop |
|---|---|---|---|---|---|---|---|
| Fat-hen, maple-leaved goosefoot, many-seeded goose foot | *Chenopodium (album, hybridum, polyspermum)* | x | x |  | x | x | x |
| Redroot pigweed, smooth amaranth, purple amaranth, prostrate pigweed | *Amaranthus (retroflexus hybridus, blitum, albus)* |  | x |  | x | x | x |
| Corn poppy | *Papaver rhoeas* | x | x |  | x | x | x |
| Thorn apple | *Datura stramonium* |  |  |  |  | x |  |
| Woundwort (annual, field) | *Stachys (annua, arvensis)* |  |  |  |  | x |  |
| Square-stalked willowherb | *Epilobium tetragonum* | x |  |  |  |  |  |
| Lesser celandine | *Ranunculus ficaria* | x |  |  |  |  |  |
| Fumitory (common, fine-leaved) | *Fumaria (officinalis parviflora)* |  |  |  |  | x |  |
| Cleavers | *Galium aparine* |  |  | x |  |  | x |
| Gallant soldier, shaggy soldier | *Galinsoga (parviflora, quadriradiata)* | x |  |  | x |  | x |
| *Geranium* | *geranium* | x |  |  |  | x |  |
| Yellow vetchling | *Lathyrus aphaca* | x |  |  | x | x |  |
| Corn gromwell | *Buglossoides arvensis* |  |  |  | x | x |  |
| Bristly ox-tongue | *Picris echioides* |  | x |  |  |  |  |
| Toad rush | *Juncus bufonius* |  |  |  | x |  |  |
| Prickly sow-thistle | *Sonchus asper* | x | x |  | x | x |  |
| Dead-nettle (red, henbit) | *Lamium (purpureum amplexicaule)* |  |  |  |  | x |  |
| Fluellen (round-leaved, sharp-leaved) | *Kickxia (spuria, elatine)* |  |  |  |  | x |  |
| Scarlet pimpernel | *Anagallis arvensis* |  |  |  |  | x |  |
| Charlock | *Sinapis arvensis* | x | x |  | x | x | x |
| Field forget-me-not | *Myosotis arvensis* | x |  |  | x |  |  |
| Common hemp-nettle | *Galeopsis tetrahit* | x |  |  | x | x | x |
| Field pepperwort | *Lepidium campestre* |  |  |  |  |  |  |
| Field pansy | *Viola arvensis* |  |  |  |  | x |  |
| Plantain (ribwort, common) | *Plantago (lanceolata, major)* | x | x |  | x |  |  |
| Bastard cabbage | *Rapistrum rugosum* | x | x |  | x | x | x |
| Wild radish | *Raphanus raphanistrum* | x |  |  | x | x | x |
| Buttercup (corn, hairy) | *Ranunculus (arvensis, sardous)* | x | x |  | x | x | x |
| Creeping buttercup | *Ranunculus repens* | x |  |  | x | x | x |
| Knotgrass | *Polygonum aviculare* |  |  | x |  | x |  |
| Groundsel | *Senecio vulgaris* | x |  |  | x | x |  |
| Large Venus's looking glass | *Legousia speculum veneris* |  |  |  |  | x |  |
| Corn spurrey | *Spergula arvensis* | x |  |  | x |  |  |
| Common chickweed | *Stellaria media* |  |  | x |  |  | x |
| Field penny-cress | *Thlaspi arvense* | x | x |  | x | x | x |
| Ivy-leaved speedwell | *Veronica hederifolia* |  |  |  | x |  |  |
| Common field-speedwell | *Veronica persica* |  |  | x |  |  |  |
| Common vetch | *Vicia sativa* | x | x |  | x | x |  |
| Creeping thistle | *Cirsium arvense* | x | x |  | x | x |  |
| Field bindweed | *Convolvulus arvensis* | x |  |  |  | x |  |

The compositions according to the invention are thus used to treat plants in large-scale farming, in particular cereals such as all species of wheat, barley, rye, triticale, millet, spelt, buckwheat, sorghum, rice, maize, fonio, finger millet, einkorn wheat, teff, foxtail millet, in open fields or between rows (targeted or localised treatment), to treat orchards, in particular peach, pear, apple, plum, cherry, hazel, apricot, almond, kiwi, between rows, to treat permanent grassland and revegetated ploughed fields in the inter-crop season, to treat grass lawns, in horticulture, particularly for weed removal from lily of the valley and strawberry plants, to treat sugar cane, to treat any genetically modified plant that is resistant to at least one of the herbicides of the composition.

The invention is illustrated in more detail by the examples below, which are given for illustrative purposes only.
Formulations Formulations of ECs (emulsifiable concentrates) obtained by mixing the ingredients of the preparations at 45° C. (Examples 1 to 5) or 85° C. (Examples 6 to 13) with a mechanical stirrer for 30 minutes. After cooling, all the formulations obtained are homogeneous, clear and of low viscosity (<1000 cps at 20° C. measured using a Brookfield DV module 3 viscometer and a needle rotating at 12 rpm). All the formulations are stable at the conventional temperatures (from 4° C. to 45° C.) for at least 3 months. In a 5% dilution in hard water, in accordance with CIPAC test MT 36, all spontaneously form an emulsion that is stable for at least 2 h at the temperature of the laboratory. At the end of 24 h the layer of cream generally observed on top of the liquid can be re-emulsified completely by simply shaking the measuring cylinder.

CIPAC test MT 36 involves diluting 5 ml of the preparation in 100 ml of standard water to give an oil-in-water emulsion after shaking the graduated measuring cylinder used for the mixture. The stability of this emulsion is then determined by measuring the volume of salted-out oil or of creamed phase after resting for 30 minutes, 2 hours and 24 hours. The standard water used is a water of hardness 342 ppm having a Ca2+/Mg2+ ratio of 4/1.

The percentages are expressed by mass relative to the total mass of the preparation.

EXAMPLE 1

| | |
|---|---|
| 2,4-D acid | 15.0% |
| 2-Hexyldecanol | 42.5% |
| C8/C12 xylosides (Dp = 1.5) | 42.5% |

EXAMPLE 2

Formula No. EC13107400

| | |
|---|---|
| 2,4-D acid | 15.0% |
| Dertol 90 (DRT) | 65.0% |
| 2-Hexyldecanol | 10.0% |
| C8/C12 xylosides (Dp = 1.5) | 10.0% |

EXAMPLE 3

| | |
|---|---|
| 2,4-D acid | 35.00% |
| Dertol 90 (DRT) | 5.85% |
| Diethyl succinate | 13.65% |
| Isodecanol | 6.82% |
| 1,3-Propanediol | 26.00% |
| Tween 80 | 5.85% |
| C8/C12 xylosides (Dp = 1.5) | 6.83% |

EXAMPLE 4

Formula No. EC13108000

| | |
|---|---|
| 2,4-D acid | 25.00% |
| Dertol 90 (DRT) | 6.75% |
| Diethyl succinate | 15.75% |
| 1,3-Propanediol | 30.00% |
| Tween 80 | 6.75% |
| XP622 (ARD) | 15.75% |

XP622 is an emulsifier based on alkyl xylosides and Guerbet alcohols.

EXAMPLE 5

Formula No. EC13108100

| | |
|---|---|
| 2,4-D acid | 15.00% |
| Dertol 90 | 10.00% |
| Diethyl succinate | 30.00% |
| 1,3-Propanediol | 20.00% |
| Radiasurf 7157 (polysorbate 80) | 10.00% |
| XP622 (ARD) | 15.00% |

XP622 is an emulsifier based on alkyl xylosides and Guerbet alcohols.

EXAMPLE 6

| | |
|---|---|
| MCPA acid | 15.0% |
| Dertol 90 (DRT) | 65.0% |
| 2-Hexyldecanol | 10.0% |
| C8/C12 xylosides (Dp = 1.5) | 10.0% |

EXAMPLE 7

| | |
|---|---|
| MCPA acid | 25.00% |
| Dertol 90 (DRT) | 6.75% |
| Diethyl succinate | 15.75% |
| 1,3-Propanediol | 30.00% |
| Tween 80 | 6.75% |
| XP622 (ARD) | 15.75% |

XP622 is an emulsifier based on alkyl xylosides and Guerbet alcohols.

EXAMPLE 8

| | |
|---|---|
| Dichlorprop acid | 15.0% |
| Dertol 90 (DRT) | 65.0% |
| 2-Hexyldecanol | 10.0% |
| C8/C12 xylosides (Dp = 1.5) | 10.0% |

EXAMPLE 9

| | |
|---|---|
| Dichlorprop acid | 25.00% |
| Dertol 90 (DRT) | 6.75% |
| Diethyl succinate | 15.75% |
| 1,3-Propanediol | 30.00% |
| Tween 80 | 6.75% |
| XP622 (ARD) | 15.75% |

XP622 is an emulsifier based on alkyl xylosides and Guerbet alcohols.

EXAMPLE 10

| | |
|---|---|
| Mecoprop acid | 15.0% |
| Dertol 90 (DRT) | 65.0% |
| 2-Hexyldecanol | 10.0% |
| C8/C12 xylosides (Dp = 1.5) | 10.0% |

EXAMPLE 11

| | |
|---|---|
| Mecoprop acid | 25.00% |
| Dertol 90 (DRT) | 6.75% |
| Diethyl succinate | 15.75% |
| 1,3-Propanediol | 30.00% |
| Tween 80 | 6.75% |
| XP622 (ARD) | 15.75% |

XP622 is an emulsifier based on alkyl xylosides and Guerbet alcohols.

EXAMPLE 12

| | |
|---|---|
| Mecoprop-P acid | 15.0% |
| Dertol 90 (DRT) | 65.0% |
| 2-Hexyldecanol | 10.0% |
| C8/C12 xylosides (Dp = 1.5) | 10.0% |

EXAMPLE 13

| | |
|---|---|
| Mecoprop-P acid | 25.00% |
| Dertol 90 (DRT) | 6.75% |
| Diethyl succinate | 15.75% |
| 1,3-Propanediol | 30.00% |
| Tween 80 | 6.75% |
| XP622 (ARD) | 15.75% |

XP622 is an emulsifier based on alkyl xylosides and Guerbet alcohols.

Open-Field Trials

Two types of trial are conducted. Firstly, selectivity trials to show the selectivity of the preparations relative to the crop being cultivated. Any changes in the behaviour of the crop (flattening, discoloration of leaves, deformation, growth retardation, etc.) in comparison to an untreated plot are recorded. This phytotoxicity is recorded on a scale of 0 to 100, based on the changes observed in comparison to the untreated plot. Above a score of 15, selectivity is no longer guaranteed. The trials are conducted in 4 repetitions and monitored up to harvesting so as to determine the potential effects on yields.

The second type of trial relates to the effectiveness of the treatments in relation to one or more specified objectives (weeds, regrowth of crops in inter-crop seasons). The trials are conducted in three repetitions. Application takes place at a specified stage (t0) of growth and the plots receiving the treatment are monitored at regular intervals (t0+10 days, t0+20 days, etc.). The effectiveness is measured as a percentage, which is calculated in terms of the number of weeds controlled (showing a high rate of phytotoxicity, degeneration and death) per $m^2$ relative to the number of weeds per $m^2$ at t0 or in the untreated crop. This information can be recorded by means of 4×0.25 $m^2$ squares per plot. In the case of crop trials, the phytotoxicity in the crop is recorded in order also to assess the selectivity at the dose used in the trial.

The trials are conducted in accordance with the conditions of Good Experimental Practice and in compliance with the methods published in France by the Commission des Essais Biologiques (CEB).

The applications are made using an electric jet sprayer carried on the experimenter's back, fitted at the front with a 3-m row of 12 or 9 nozzles (25 or 33 cm apart). The nozzles used are anti-drift Teejet® or Albuz® nozzles delivering a jet at an angle of 80°.

The preparations according to the invention are compared with standard commercial products used in their approved doses. As the trials are conducted in France, these approved doses are those prescribed by law and published in "Le catalogue des produits phytopharmaceutiques et de leurs usages des matieres fertilisantes et des supports de culture homologues en France", which is available online from: http://e-phy.agriculture.gouv.fr/.

Selectivity

The examples below illustrate the possible effects of loss of selectivity in preparations of 2,4-D acid according to the invention in the approved or conventionally recommended doses for 2,4-D dimethylamine salt and the selectivity compliance at a half and a quarter of that dose.

EXAMPLE 14

Selectivity on Wheat

The formulation of example 2 (EC 13107400) is used at a rate of 1.4, 2.8 and 5.6 l/ha or 210, 420 and 840 g/ha of 2,4-D acid and is compared with a commercial preparation containing 600 g/l acid equivalent of 2,4-D dimethylamine salt (ref. C600) and used in its approved dose of 1.4 l/ha or 840 g/ha of 2,4-D acid equivalent and with the reference preparation (ref. M) containing 180 g/ha of ioxynil acid equivalent and 290 g/ha of mecoprop-P acid equivalent in its approved dose of 2.0 l/ha or 360 g/ha of ioxynil acid equivalent and 580 g/ha of mecoprop-P equivalent.

The table below sets out the results obtained on soft winter wheat (variety Haussmann), treated on 26 April in the Marne département (51-F) using a manual sprayer delivering 200 l/ha.

| | g/ha acid eq. | Phytotoxicity (%, visual, 43 days after treatment) | Yield (Q/ha, 95 d after treatment) |
|---|---|---|---|
| Control | | 0 | 124.1 |
| EC 13107400 | 210 | 0 | 123.3 |
| EC 13107400 | 420 | 0 | 122.8 |
| EC 13107400 | 840 | 5 | 121.6 |
| Ref. C600 | 840 | 0 | 123.6 |
| Ref. M | 940* | 4.3 | 120.9 |

*Mixture of ioxynil and mecoprop-P

The formulation of Example 2 shows slight signs of phytotoxicity on wheat at 840 g/ha. Used in half or a quarter of the approved dose of the equivalent dimethylamine salts, complete selectivity compliance is achieved.

EXAMPLE 15

Selectivity on Maize

The formulation of Example 2 (EC 13107400) is used at a rate of 2, 4 and 8 l/ha or 300, 600 and 1200 g/ha of 2,4-D acid and compared with a commercial preparation (ref. A600) containing 600 g/l acid equivalent of 2,4-D dimethylamine salt used in its approved dose of 2.0/ha or 1200 g/ha of 2,4-D acid equivalent.

The table below sets out the results obtained on maize (variety Storm), treated on 27 May in the Somme département (80-F) using a manual sprayer delivering 200 l/ha.

| | g/ha acid eq. | Phytotoxicity (%, visual, 60 days after treatment) | Yield (Q/ha, 150 d after treatment) |
|---|---|---|---|
| Control | | 0 | 121.04 |
| EC 13107400 | 300 | 0 | 117.45 |
| EC 13107400 | 600 | 0 | 101.40 |
| EC 13107400 | 1200 | 30 | 76.20 |
| Ref. A600 | 1200 | 0 | 110.18 |

The formulation of Example 2 shows signs of phytotoxicity on maize at 1200 g/ha. Used in half or a quarter of the approved dose of the equivalent dimethylamine salts, complete selectivity compliance is achieved.

Effectiveness

EXAMPLE 16

Treatment in Open Fields and in the Inter-Crop Season

The formulation of Example 2 (EC13107400) is compared with a commercial preparation (ref. A600) containing 600 g/l acid equivalent of 2,4-D dimethylamine salt used in its approved dose of 2.0 l/ha or 1200 g/ha of 2,4-D acid equivalent to treat maize infected with bindweed (25% coverage) and with this same preparation used at a rate of 1 l/ha to apply a dose of 600 g/ha acid equivalent to treat fields in the inter-crop season, on the destruction of regrowth of colza and opium poppy.

The formulations of Examples 4 and 5 (EC13108000 and EC13108100) are also compared with this same preparation in a dose of 600 g/ha acid equivalent for the treatment of regrowth of colza and opium poppy in the inter-crop season.

The formulations of Examples 2, 4 and 5 are used in half the dose (D/2) and a quarter of the dose (D/4) of the commercial reference. The results are shown as a percentage of the relative effectiveness in comparison with the results obtained with the reference preparation in the full dose (actual effectiveness adjusted to 100).

|  | Dose in acid equivalent/ha | Hedge bindweed (CALCSECV), 14 days after treatment, 25% coverage (control) | Regrowth of colza (BRSNNH1), mean of 4 trials, 21 days after treatment | Opium poppy (PAPSO), 28 days after treatment, 85% coverage (control) |
|---|---|---|---|---|
| Ref. A600 | D | 100 | 100 | 100 |
| EC 13107400 | D/2 | 98.4 | 119 | 145.5 |
| EC 13107400 | D/4 | 81.4 | 95.9 | 78.7 |
| EC 13108000 | D/2 |  | 125.4 | 151.5 |
| EC 13108000 | D/4 |  | 98.5 | 96.9 |
| EC 13108100 | D/2 |  | 128.6 | 151.5 |
| EC 13108100 | D/4 |  | 95.9 | 96.9 |

The results obtained show that in a half-dose the effectiveness of the formulations of Examples 2, 4 and 5 prepared according to the invention is far superior to that of the commercial formulation in the full dose. In a quarter-dose the results for the formulations of Examples 2, 4 and 5 are approximately equivalent to those for the commercial formulation in the full dose.

Example 15 also shows that in a half-dose and a quarter-dose the selectivity in respect of maize is fully compliant.

EXAMPLE 17

Treatment of Lawns

The formulation of Example 2 (EC13107400) is compared to a commercial preparation (ref. A600) containing 600 g/l acid equivalent of 2,4-D dimethylamine salt used in its approved dose of 1.2 l/ha or 720 g/ha of 2,4-D acid equivalent to treat lawns against broadleaf weeds (ribwort plantain, white clover and black medick).

The formulation according to the invention is used in half and a quarter of the dose (D/2 and D/4) of the commercial reference. The results are expressed on a scale of effectiveness from 0 to 10 with a letter (a to c) representing the statistical group to which they belong (two results with the same letter belong to the same group).

|  | Dose in acid equivalent/ha | Ribwort plantain (PLALA) 91 days after treatment Score of 0-10 | White clover (TRFRE) 91 days after treatment Score of 0-10 | Black medick (MEDLU) 91 days after treatment Score of 0-10 |
|---|---|---|---|---|
| Ref. A600 | D = 720 g/ha acid equivalent | 5.0 (b) | 0.5 (c) | 9.8 (a) |
| EC 13107400 | D | 9.0 (a) | 4.5 (b) | 10.0 (a) |
| EC 13107400 | D/2 | 4.5 (b) | 3.5 (b) | 8.0 (a) |
| EC 13107400 | D/4 | 2.0 (c) | 0.0 (c) | 4.5 (b) |

The results obtained show the effectiveness of the formulation of Example 2 in dose D and D/2 in comparison to the commercial formulation. The control of phytotoxicity on the lawn illustrates the selectivity compliance across all the trials.

EXAMPLE 18

Arboriculture 18.1: The formulation of Example 2 (EC13107400) is compared to a commercial preparation (ref. C600) containing 600 g/l acid equivalent of 2,4-D dimethylamine salt used in its approved dose of 1.6 l/ha or 960 g/ha of 2,4-D acid equivalent to treat the bases of apple trees (Belle de Boskoop) against broadleaf weeds (ribwort plantain).

The formulation according to the invention is used in half the dose (D/2) of the commercial reference. The results are shown as a percentage of the relative effectiveness in comparison with the results obtained with the reference preparation in the full dose (actual effectiveness adjusted to 100).

|  | Dose in acid equivalent/ha | Ribwort plantain (PLALA) 20 days after treatment | Ribwort plantain (PLALA) 39 days after treatment | Ribwort plantain (PLALA) 67 days after treatment |
|---|---|---|---|---|
| Ref. C600 | D = 960 g/ha acid equivalent | 100 | 100 | 100 |
| Ref. C600 | D/2 | 54.5 | 46.2 | 67.9 |
| EC 13107400 | D | 131.6 | 142.5 | 117.8 |
| EC 13107400 | D/2 | 81.7 | 73.2 | 92.7 |

The results obtained show the effectiveness of the formulation of Example 2 in dose D and D/2 in comparison to the commercial formulation.

18.2: The formulation of Example 2 (EC13107400) and the formulation of Example 4 (EC13108000) are compared to a commercial preparation (ref. A600) containing 600 g/l acid equivalent of 2,4-D dimethylamine salt used in its approved dose of 1.6 l/ha or 960 g/ha of 2,4-D acid equivalent to treat the bases of apple trees (Golden Delicious) against broadleaf weeds (scarlet pimpernel, daisy, hairy bittercress, sun spurge, ribwort plantain, hoary plantain, perennial sow-thistle, groundsel, dandelion, field speedwell).

The formulations according to the invention are used in half the dose (D/2) of the commercial reference. The results are shown as a percentage of the relative effectiveness in comparison with the results obtained with the reference preparation in the full dose (actual effectiveness adjusted to 100).

|  | Dose in acid equivalent/ha | All broadleaf weeds (TTDICDI) 13 days after treatment | All broadleaf weeds (TTDICDI) 75 days after treatment | All broadleaf weeds (TTDICDI) 106 days after treatment |
|---|---|---|---|---|
| Ref. A600 | D = 960 g/ha acid equivalent | 100 | 100 | 100 |
| EC 13107400 | D/2 | 80.8 | 100 | 110 |
| EC 13108000 | D/2 | 95.1 | 117.7 | 100 |

The results obtained show the effectiveness of the formulations of Example 2 and Example 4 in half the dose in comparison to the commercial formulation.

The invention claimed is:

1. A herbicide composition comprising from 1 to 65% by mass of at least one phenoxyalkanoic acid herbicide in free acid form, at least one benzoic acid herbicide in free acid form or combination thereof relative to the total mass of the composition;
   20 to 98% by mass of one or more solvents or oils relative to the total mass of the composition;
   1 to 65% by mass of one or more surfactants relative to the total mass of the composition comprising at least one surfactant selected from a molecule of formula $ROX_n$ where R is a linear or branched aliphatic group, saturated or unsaturated having 6 to 22 carbon atoms, X is a pentose radical, and n is between 1 and 3;
   wherein the composition comprises less than 3% water by mass relative to the total mass of the composition.

2. The composition according to claim 1, contains from 0 to less than 1% by mass of water.

3. The composition according to claim 1, that is free from a herbicide from a family other than the two families.

4. The composition according to claim 3, contains the at least one phenoxyalkanoic acid selected from 2,4-D (2,4-dichlorophenoxyacetic acid), 2,4-DB (2-(2,4-dichlorophenoxy)butyric acid), dichlorprop ((RS)-2-(2,4-dichlorophenoxy)propionic acid), dichlorprop-P ((R)-2-(2,4-dichlorophenoxy)propionic acid), MCPA (4-chloro-o-tolyloxyacetic acid), MCPB (4-(4-chloro-o-tolyloxy)butyric acid), mecoprop ((RS)-2-(4-chloro-o-tolyloxy)propionic acid), and mecoprop-P ((R)-2-(4-chloro-o-tolyloxy)butyric acid) and the at least one benzoic acid selected from Dicamba (3,6-dichloro-o-anisic acid), and 2,3,6-TBA (2,3,6-trichlorobenzoic acid).

5. The composition according to claim 1, wherein the one or more solvents or oils are chosen from vegetable oils, esters of vegetable oils, esters of vegetable fatty acids, esters of acids obtained by fermentation of vegetable biomass, terpenes, synthetic or semi-synthetic alcohols derived from vegetable oils, alcohols obtained by fermentation of vegetable biomass and synthetic or semi-synthetic readily biodegradable vegetable solvents.

6. The composition according to claim 1, contains, as the one or more solvents or oils, a terpene alcohol, a succinic acid diester, a diol or an alcohol.

7. The composition according to claim 1, wherein the at least one surfactant of formula ROXn, in which R is a linear or branched aliphatic group, saturated or unsaturated and having 6 to 22, X is a pentose radical, and n is between 1 and 3, and at least one non-ionic, anionic, cationic or amphoteric co-surfactant.

8. The composition according to claim 7, contains from 1 to 25% of the at least one non-ionic, anionic, cationic or amphoteric co-surfactants.

9. The composition according to claim 4, wherein X is xylose.

10. The composition according to claim 4, wherein the aliphatic group has from 8 to 16 carbon atoms.

11. The composition according to claim 7 which contains from 10 to 45% of said at least one herbicide, from 25 to 85% of one or more said solvents or oils, and from 5 to 45% of one or more said surfactants.

12. The composition according to claim 4, wherein n is between 1 and 1.8.

13. A method of preparation of a herbicide preparation the composition according to claim 1 is mixed with water, in which the amount of water added represents from 75 to 99.999%, of the total mass of the preparation.

14. A method for controlling or preventing the growth of weeds in crops of cereals selected from species of wheat, barley, rye, triticale, millet, spelt, buckwheat, sorghum, rice, maize, fonio, finger millet, einkorn wheat, teff, foxtail millet, in orchards, peach, pear, apple, plum, cherry, hazel, apricot, almond, and kiwi, in permanent grassland and revegetated ploughed fields in inter-crop seasons, on grass lawns, in horticulture or in fields of sugar cane, wherein the composition prepared in accordance with any one of claims 1-4, 5-7, 8, 9-12 is applied directly to the crops or in a targeted manner directly to the weeds.

* * * * *